United States Patent [19]
Biller et al.

[11] Patent Number: 6,087,349
[45] Date of Patent: Jul. 11, 2000

[54] METHOD FOR BLOCKING NEOPLASTIC TRANSFORMATION OF CELLS INDUCED BY RAS ONCOGENES

[75] Inventors: Scott A. Biller, Ewing; Mariano Barbacid, Lawrenceville; Eric M. Gordon, Pennington; David R. Magnin, Hamilton; Chester A. Meyers, Medford, all of N.J.; Veeraswamy Manne, Yardley, Pa.

[73] Assignee: E. R. Squibb & Sons, Inc., Princeton, N.J.

[21] Appl. No.: 09/081,972

[22] Filed: May 6, 1998

Related U.S. Application Data

[63] Continuation of application No. 08/740,831, Nov. 4, 1996, abandoned, which is a continuation of application No. 07/774,957, Oct. 11, 1991, abandoned.

[51] Int. Cl.$^7$ ........................... A01M 57/10; A01M 57/00
[52] U.S. Cl. ........................... 514/108; 514/102; 514/109
[58] Field of Search ................................. 514/102, 109, 514/108

[56] References Cited

U.S. PATENT DOCUMENTS

| | | | |
|---|---|---|---|
| 4,871,721 | 10/1989 | Biller | 514/102 |
| 5,025,003 | 6/1991 | Biller | 514/120 |
| 5,338,731 | 8/1994 | Breuer et al. | 514/108 |

OTHER PUBLICATIONS

Hancock, et al, Jun. 30, 1989, Cell 57:1167–1177.
Casey, et al, Nov. 1989, Proc. Natl. Acad. Sci. U.S.A. 86:8323–8327.
Schafer, et al, Jul. 28, 1989, Science 245:379–385.
Goldstein and Brown, FEb. 1, 1990, Nature 343:425–430.
Rine and Kim, "A Role for Isoprenoid Lipids in the Localization and Function of an Oncoprotein," The New Biologist, vol. 2, No. 3 (Mar.) 1990: pp. 219–236.
Gibbs, "Ras C–Terminal Processing Enzymes–New Drug Targets," Cell, vol. 65, 1–4, Apr. 5, 1991.
Reiss et al, "Inhibition of Purified p 21$^{ras}$ Farnesyl:Protein Transferase by Cyc–AAX Tetrapeptides," Cell, vol. 62, 81–88, Jul. 13, 1990.
Touchette, "Cholesterol and Cancer Studies Get a Rise Out of Yeast," The Journal of NIH Research, Apr. 1990, vol. 2, 61–65.
Lowy et al, "New Clue to Ras lipid glue," Nature vol., 341, pp. 384–385, Oct. 5, 1989.
Schafer et al, "Enzymatic Coupling of Cholesterol Intermediates to a Mating Pheromone Precursor and to the Ras Protein," Science, vol. 249, pp. 1133–1139. (1991).
Glomset et al, "The prenylation of proteins," Current Opinion in Lipidology 1991, 2:118–124.

*Primary Examiner*—Theodore J. Criares
*Attorney, Agent, or Firm*—Burton Rodney; John M. Kilcoyne

[57] ABSTRACT

A method is provided by blocking or preventing the prenylation of CAAX box containing proteins including ras oncogene products thereby preventing and/or treating ras-related tumors which includes the step of administering a therapeutically effective amount of a protein-prenyl transferase inhibitor.

14 Claims, No Drawings

METHOD FOR BLOCKING NEOPLASTIC TRANSFORMATION OF CELLS INDUCED BY RAS ONCOGENES

This application is a continuation of application Ser. No. 08/740,831, filed Nov. 4, 1996, now abandoned, which in turn is a continuation of application Ser. No. 07/774,957, filed Oct. 11, 1991, also abandoned.

FIELD OF THE INVENTION

The present invention relates to a method for treating and/or preventing tumors by blocking the prenylation of CAAX box containing proteins, including ras oncogene products, by administering a therapeutic amount of a protein-prenyl transferase inhibitor.

BACKGROUND OF THE INVENTION

The products of ras genes comprise a family of guanine nucleotide binding proteins that are involved in the control of eukaryotic cell proliferation. Specific point mutations result in ras oncoproteins which have the ability to neoplasticly transform mammalian cells, and activated ras genes have been observed in at least 10% of all human tumors. Their incidence in certain malignancies, such as in colorectal and pancreatic cancers, is far greater.

Genetic studies first established that ras proteins, referred to as ras p21, must be formed by post-translational modification of a precursor protein with a defined carboxy-terminal structure, in order to exert their biological function. This structure, known as the CAAX box, is formed of a conserved cysteine residue located four amino acid-residues from the carboxy terminus, which in the case of ras is position 186 (except in the K-ras4B p21 protein, in which cysteine is located at position 185), followed by two aliphatic amino acids and any carboxy-terminal amino acid residue. Mutations affecting the basic CAAX box structure of oncogenic ras p21 proteins completely abolish their transforming activity, presumably by impeding their interaction with the inner side of the plasma membrane. Such interaction requires a series of post-translational modifications within the CAAX box motif which include (a) farnesylation of the cys residue of the CAAX box; (b) cleavage of the three carboxy-terminal amino acid residues; and (c) methylation of the free carboxyl group generated in the resulting carboxy-terminal farnesyl-cysteine residue. The interaction of these farnesylated ras p21 proteins with cellular membranes in some cases is further strengthened by palmitoylation of neighboring upstream cysteine residues. See Hancock, et al, Jun. 30, 1989, Cell 57:1167–1177; and Casey, et al, November 1989, Proc. Natl. Acad. Sci. U.S.A. 86:8323–8327.

Recent studies have suggested that the donor of the farnesyl residue present in ras p21 proteins is farnesyl pyrophosphate (FPP), a precursor also in the biosynthesis of cholesterol. The transfer of the farnesyl group from FPP, the donor molecule, to ras proteins is mediated by the enzyme, protein-farnesyl transferase (FT).

Treatment of S. cerevisiae cells or Xenopus oocytes with inhibitors of HMG-CoA reductase, the enzyme responsible for the synthesis of mevalonic acid, the precursor of isoprenoid compounds, blocks the function of ras proteins in these cells. These results have raised the possibility of using inhibitors of cholesterol biosynthesis, that is, HMG CoA reductase inhibitors, to block neoplastic transformation induced by ras oncogenes. See, Schafer, et al, Jul. 28, 1989, Science 245:379–385; and Goldstein and Brown, Feb. 1, 1990, Nature 343:425–430.

Rine and Kim, "A Role for Isoprenoid Lipids in the Localization and Function of an Oncoprotein," The New Biologist, Vol. 2, No. 3 (March), 1990: pp 219–236, disclose at pages 222–223 that "lovastatin [also known as Mevacor], compactin, and related drugs that have been developed for the treatment of hypercholesterolemia act by inhibiting 3-hydroxy-3-methylglutaryl coenzyme A reductase (HMG-CoA reductase), the enzyme that catalyzes the rate-limiting step in the synthesis of cholesterol and all other polyisoprenoids . . . . The drugs were tested in the Xenopus oocyte assay . . . for their ability to pharmacologically suppress activated H-Ras$^{val12}$ . . . . These experiments pinpointed farnesyl pyrophosphate as the likely donor molecule for farnesylation of Ras protein, and suggested a rationale for a novel pharmacological route to block the action of this important human oncoprotein."

"Earlier work had already provided evidence that inhibition of isoprenoid synthesis by use of inhibitors of 3-hydroxy-3-methylglutaryl (HMG)-CoA reductase could slow the growth of tumors in animals. In particular, continuous, high levels of lovastatin caused substantial growth inhibition of a mouse neuroblastoma . . . . Although the oncogene(s) responsible for this tumor has not yet been identified and the dosage required to suppress the tumor was rather high, this study does support the notion that protein prenyl transferase(s) responsible for Ras modification might serve as useful targets for chemotherapy . . . ."

U.S. patent application Ser. No. 520,570 filed May 8, 1990, by Barbacid et al discloses protein-farnesyl transferase (FT) assays for identifying compounds that block the farnesylation of ras oncogene products. The Barbacid et al invention is based, in part, on the discovery and identification of the FT enzyme which catalyzes the transfer of the farnesyl group from the donor, farnesyl pyrophosphate (FPP), to the ras p21 Cys$^{186}$ residue. Farnesylation of ras proteins is required for their attachment to the inner cell membrane and biological activity. Farnesylation of ras oncogene products is required for ras mediated transforming activity. Because the assays of the Barbacid et al invention are designed to target a step subsequent to the synthesis of FPP (in the cholesterol chain), they allow for the identification of compounds that interfere with farnesylation of the ras oncogene products and inhibit their transforming activity, yet do not interfere with the synthesis of FPP, a precursor in the synthesis of cholesterol, ubiquinones, dolichols and Haem A. Therefore, FT inhibitory compounds that do not disrupt important cellular pathways which require FPP may be identified using the Barbacid et al assay.

Squalene synthetase is a microsomal enzyme which catalyzes the reductive dimerization of two molecules of farnesyl pyrophosphate (FPP) in the presence of nicotinamide adenine dinucleotide phosphate (reduced form) (NADPH) to form squalene (Poulter, C. D.; Rilling, H. C., in "Biosynthesis of Isoprenoid Compounds," Vol. I, Chapter 8, pp. 413–441, J. Wiley and Sons, 1981, and references therein). This enzyme is the first committed step of the de novo cholesterol biosynthetic pathway.

Squalene synthetase inhibitors which block the action of squalene synthetase (after the formation of farnesyl pyrophosphate) are disclosed in U.S. Pat. Nos. 4,871,721 and 5,025,003, U.S. application Ser. No. 501,204, filed Mar. 29, 1990, and U.S. application Ser. No. 699,429, filed May 13, 1991.

DESCRIPTION OF THE INVENTION

In accordance with the present invention, it has been found that post-translational modification of CAAX box containing proteins may be inhibited by administering a protein-prenyl transferase inhibitor which inhibits the transfer of the prenyl group [such as farnesyl (in the case of ras oncogene products), geranyl or geranylgeranyl] to the cysteine of the CAAX box by the protein-prenyl transferase enzyme. The protein-prenyl transferase inhibitor will block the protein-prenyl transferase enzyme from catalyzing the transfer of the prenyl group (for example, farnesyl, geranyl or geranylgeranyl) from the prenyl pyrophosphate to the cys residue of the CAAX box, such as the ras p21 cys, or to the CAAX box cysteine of other CAAX box containing proteins. In the case of ras p21 oncogene products, inasmuch as the cys will not be farnesylated it cannot effect interaction of the ras protein with the membrane so that neoplastic transformation of the cell will be prevented. In this manner protein-prenyl transferase inhibitors prevent neoplastic transformation of the cell, thereby acting as an anti-cancer agent for the treatment of and/or prevention of ras-related tumors.

Examples of CAAX box containing proteins which have been demonstrated or are believed to undergo prenylation include, but are not limited to, nuclear lamins, α or γ subunits of heterotrimeric G-proteins, γ-subunits of retinal transducin, G25K and K-rev p21, and protein families including rho, rap, rac, ral, and rab.

Thus, the present invention resides in a method for blocking or preventing the prenylation of CAAX box containing proteins such as ras oncogene products, and thereby inhibit disease promoting effects of the CAAX box containing protein or more specifically prevent and/or treat ras-related tumors, by administering to a patient in need of treatment a therapeutic amount of a protein-prenyl transferase inhibitor.

The protein-prenyl transferase inhibitors, unlike HMG CoA reductase inhibitors, will interfere with prenylation of the ras oncogene products and inhibit their transforming activity, yet may or may not interfere with the synthesis of FPP, a precursor in the synthesis of ubiquinones, dolichols and Haem A.

The activity of the protein-prenyl transferase inhibitors in blocking the protein-prenyl (e.g. farnesyl, geranyl or geranylgeranyl) transferase from catalyzing the transfer of the prenyl group (e.g. farnesyl, geranyl or geranylgeranyl) from the prenyl pyrophosphate to the cys residue of the CAAX box may be assayed by the procedure described in U.S. application Ser. No. 520,570 filed May 8, 1990, by Barbacid et al, the disclosure of which is incorporated herein by reference.

Protein-prenyl transferase inhibitors suitable for use herein include compounds disclosed in U.S. application Ser. No. 699,429 filed May 13, 1991, by Biller et al. These protein-prenyl transferase inhibitors have the following structure

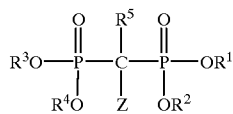

I wherein $R^1$, $R^2$, $R^3$ and $R^4$ are the same or different and are H, alkyl, a metal ion or a prodrug ester;

$R^5$ is H, halogen or lower alkyl;

Z a lipophilic group containing at least 6 carbons and can be substituted alkenyl wherein the alkenyl group contains from 7 to 25 carbon atoms in the chain and from 1 to 4 double bonds; substituted alkynyl containing 1 to 4 triple bonds; mixed alkenyl-alkynyl containing 1 to 3 double bonds and 1 to 3 triple bonds and wherein alkenyl and/or alkynyl may be substituted or unsubstituted; or a substituted phenylalkyl group of the structure

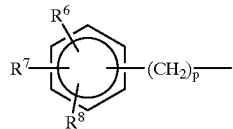

wherein $(CH_2)_p$ contains from 1 to 15 carbons, preferably 2 to 12 carbons, in the chain and may include 0, 1, 2 or 3 double bonds and/or 0, 1, 2 or 3 triple bonds in the normal chain, and/or may include 0, 1, 2 or 3 substituents; and $R^6$, $R^7$ and $R^8$ are the same or different and are H, alkyl containing 1 to 40 carbons, preferably from 3 to 15 carbons, alkoxy containing 1 to 40 carbons, preferably from 3 to 15 carbons, alkenyl containing 2 to 40 carbons, preferably from 3 to 15 carbons, alkenyloxy containing 2 to 40 carbons, preferably from 3 to 15 carbons, alkynyl containing 2 to 40 carbons, preferably from 3 to 15 carbons, alkynyloxy containing 2 to 40 carbons, preferably from 3 to 15 carbons, aryloxy, hydroxy, halogen, nitro, amino, thiol, alkylthio, arylthio, alkylsulfinyl, arylsulfinyl, alkylsulfonyl, arylsulfonyl, carboxy, alkoxycarbonyl, aminocarbonyl, alkylcarbonyloxy, arylcarbonyloxy, arylcarbonylamino or alkylcarbonylamino, at least one of $R^6$, $R^7$ and $R^8$ being alkenyl, alkenyloxy, alkynyl or alkynyloxy; and wherein the total number of carbons in the substituted phenylalkyl group exceeds 10 carbons.

The terms "substituted alkenyl" and "substituted alkynyl" as employed herein with respect to Z refers to alkenyl or alkynyl substituted with 1 to 4 groups which may be alkyl, alkenyl, alkynyl, halogen, hydroxy, alkoxy, alkenyloxy, alkynyloxy, aryl and/or cycloalkyl.

The $(CH_2)_p$ group may contain one or more alkyl, alkoxy, alkenyl, alkynyl, hydroxy and/or halogen substituents.

Preferred embodiments of formula I protein-prenyl transferase inhibitors have the structure

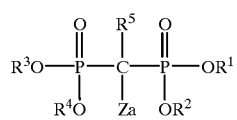

II wherein $R^1$, $R^2$, $R^3$, $R^4$ and $R^5$ are as defined above and Za is substituted alkenyl which includes from 1 to 4 double bonds and is substituted with from 1 to 4 alkyl groups.

In addition, other protein-prenyl transferase inhibitors suitable for use herein and disclosed in application Ser. No. 699,429 have the structure

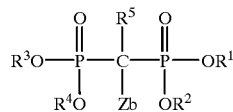

III wherein Zb is

-continued

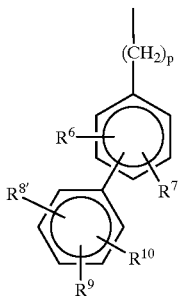

wherein $R^1$, $R^2$, $R^3$, $R^4$, $R^5$, $R^6$, $R^7$ and $(CH_2)_p$ are as defined hereinbefore, except that $R^6$ and $R^7$ may be any one of the groups included under the definition $R^6$ and $R^7$, set out hereinbefore, without limitation; $R^{8'}$, $R^9$ and $R^{10}$ are the same or different and are as defined hereinbefore with respect to $R^6$ and $R^7$, without limitation.

Preferred are compounds of formula III wherein the $R^{8'}$, $R^9$, $R^{10}$-substituted phenyl is para to the $R^6$, $R^7$-phenylene. These compounds have been found to inhibit cholesterol biosynthesis when administered orally.

In another embodiment of the present invention, compounds which are protein-prenyl transferase inhibitors (disclosed in Ser. No. 699,429) may be employed which have the structure

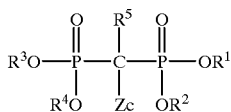

IV wherein $R^1$, $R^2$, $R^3$, $R^4$ and $R^5$ are as defined herein-before and Zc is alkyl wherein the alkyl group contains from 9 to 14 carbons in the normal chain and is substituted with 1, 2, 3 or 4 alkyl groups.

Still another embodiment of compounds which are protein-prenyl transferase inhibitors (disclosed in Ser. No. 699,429) have the structure

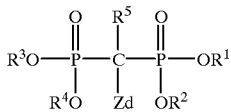

V wherein Zd is

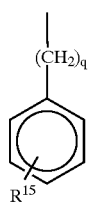

wherein $R^1$, $R^2$, $R^3$, $R^4$ and $R^5$ are as defined herein-before and $(CH_2)_q$ contains at least 2 carbons in the chain and may include 0, 1, 2 or 3 double bonds and/or 0, 1, 2 or 3 triple bonds in the normal chain, preferably 3 to 7 carbons in the normal chain, and may include one or more alkyl, alkenyl, alkynyl, alkoxy, hydroxy and/or halogen substituents; and $R^{15}$ is alkyl containing from 2 to 20 carbons, and preferably is in the para position, and the total number of carbons in Zd exceeds 10.

Other protein-prenyl transferase inhibitors suitable for use herein are compounds disclosed in U.S. application Ser. No. 501,204 filed Mar. 29, 1990, by Biller et al and have the following structure

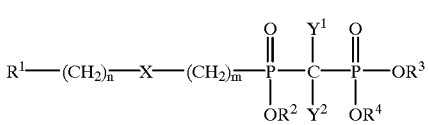

VI wherein m is 0, 1, 2 or 3; n is 0, 1, 2, 3 or 4; $Y^1$ and $Y^2$ are H or halogen, preferably H or F; $R^2$, $R^3$ and $R^4$ are independently H, metal ion, $C_1$ to $C_8$ alkyl or $C_3$ to $C_{12}$ alkenyl; X is O, NH,

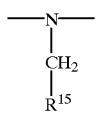

or S (wherein
$R^{15}$ is H or $C_1$ to $C_5$ alkyl); $R^1$ is $R^5$—$Q^1$—$Q^2$—$Q^3$— wherein $Q^1$, $Q^2$ and $Q^3$ are independently:

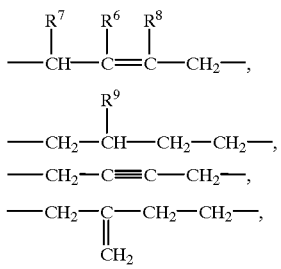

or a bond, with the stipulation that if $Q^1$ is a bond, then $Q^2$ and $Q^3$ must be bonds, and if $Q^2$ is a bond, then $Q^3$ is a bond; $R^6$ is H, lower alkyl, halo or haloalkyl (e.g. $CH_2F$, $CF_3$); $R^7$ is H, halogen, lower alkyl or alkylthio; $R^8$ is H, halogen, trimethylsilyl or lower alkyl; $R^9$ is H, or lower alkyl;

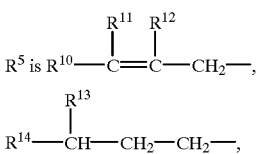

$R^{16}$—C≡C—$CH_2$-(wherein $R^{16}$ is lower alkyl or H),

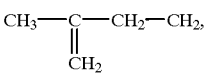

or $CH_3$ $(CH_2)_p$— where p is 2 to 7;
$R^{10}$ and $R^{11}$ are independently hydrogen, lower alkyl such as methyl or ethyl, halogen, lower alkenyl or haloalkyl or $R^{10}$ and $R^{11}$ can be taken together to form $(CH_2)_s$, where s is 2 to 7; $R^{12}$ is hydrogen, lower alkyl, halogen or lower alkenyl; $R^{13}$ and $R^{14}$ are independently lower alkyl such as methyl or ethyl; with the provisos that if all of $Q^1$, $Q^2$ and $Q^3$ are bonds, then $R^{10}$ and $R^{11}$ cannot both be H, and $R^5$ cannot be $CH_3(CH_2)_p$—, with $p \leq 4$; if m is o, X is other than S; and if m is o and X is O, then n is 1, 2, 3 or 4, including all stereoisomers thereof.

The term "lower alkenyl" or "alkenyl" as used above by itself or as part of another group refers to straight or branched chain radicals of 2 to 12 carbons, preferably 3 to 6 carbons in the normal chain, which include one double bond in the normal chain, and which may include an aryl or alkyl substituent, such as vinyl, 2-propenyl, 2-butenyl, 3-phenyl-2-propenyl, 2-pentenyl, 2-hexenyl, 2-heptenyl, 2-octenyl, 2-nonenyl, 2-decenyl, 2-undecenyl, 2-dodecenyl and the like.

Preferred are those compounds of formula VI which have the following formula: VII

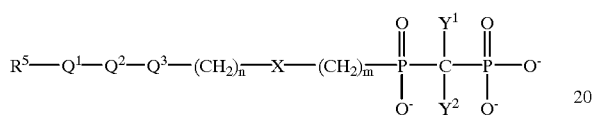

wherein $R^5$ is

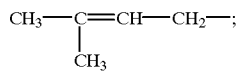

$Q^3$ is a bond;

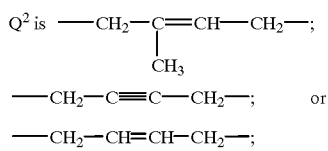

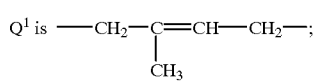

n is O or 1; m is 1 or 2; X is O and $Y^1$ and $Y^2$ are each H or F, in the form of the salts or acid.

In addition, preferred are those compounds of formula VI which have the following structure VIA-A

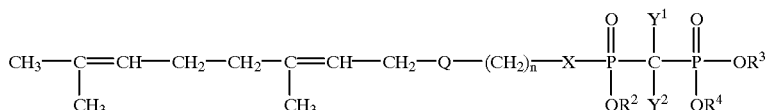

wherein Q is

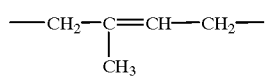

or a bond; n is 1 or 2;

X is O, $Y^1$ and $Y^2$ are each H or each F; $R^2$, $R^3$ and $R^4$ are alkyl, H or metal ions; or X is NH and n is 0.

In addition, protein-prenyl transferase inhibitors which may be employed herein include compounds disclosed in U.S. Pat. No. 5,025,003 to Biller and have the following structure

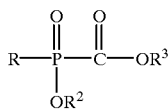

VIII wherein $R^2$ is a metal ion, lower alkyl or H;

$R^3$ is a metal ion or lower alkyl;

R is $R^1$—$(CH_2)_n$—, $R^1$—$(CH_2)_m$O— or $R^1$—$(CH_2)_m$OCH$_2$—, wherein n is 1 to 4, m is 0 to 3; and $R^1$ is $R^5$—$Q^1$—$Q^2$—$Q^3$— wherein $Q^1$, $Q^2$ and $Q^3$ are independently:

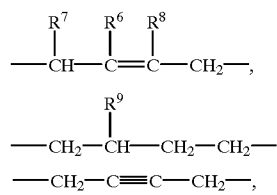

or a bond, with the stipulation that if $Q^1$ is a bond, then $Q^2$ and $Q^3$ must be bonds, and if $Q^2$ is a bond, then $Q^3$ is a bond; $R^6$ is H, lower alkyl, fluoro or fluoroalkyl (e.g., $CH_2F$, $CF_3$); $R^7$ is H, fluoro, lower alkyl or alkylthio; $R^8$ is H, fluoro, trimethylsilyl or lower alkyl; $R^9$ is H, or lower alkyl;

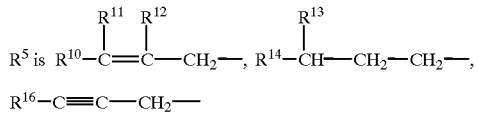

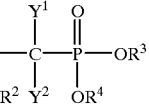

(wherein $R^{16}$ is lower alkyl or H), or $CH_3(CH_2)_p$— where p is 2 to 7; $R^{10}$ and $R^{11}$ are independently hydrogen, lower alkyl such as methyl or ethyl, fluoro, lower alkenyl or fluoroalkyl or $R^{10}$ and $R^{11}$ can be taken together to form $(CH_2)_s$, where s is 2 to 7; $R^{12}$ is hydrogen, lower alkyl, fluoro or lower alkenyl; $R^{13}$ and $R^{14}$ are independently lower alkyl such as methyl or ethyl; with the proviso that if all of $Q^1$, $Q^2$ and $Q^3$ are bonds, then $R^{10}$ and $R^{11}$ cannot both be H, and $R^5$ cannot be $CH_3(CH_2)_p$—, with p<4, including all stereoisomers thereof.

The term "lower alkenyl" or "alkenyl" as used herein is defined hereinbefore.

Preferred are those compounds of formula VIII wherein $R^1$ is

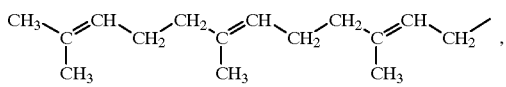

n is 1, 2 or 3, m is 1 or 2, $R^2$ is H or a metal ion, and $R^3$ is lower alkyl, a metal ion or H.

Other protein-prenyl transferase inhibitors suitable for use herein include compounds disclosed in U.S. Pat. No. 4,871,721 to Biller and have the following structure:

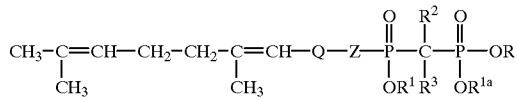

wherein Q is

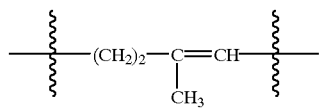

or a bond;

Z is —(CH$_2$)$_n$— or —(CH$_2$)$_p$—CH=CH—(CH$_2$)$_m$—, wherein n is 1 to 5; p is 0, 1 or 2; m is 0, 1 or 2;

R, $R^1$ and $R^{1a}$ may be the same or different and are H, lower alkyl or a metal ion; and $R^2$ and $R^3$ may be the same or different and are H or halogen.

Preferred are those compounds of formula IX which have the following structure

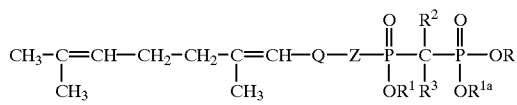

wherein Q is

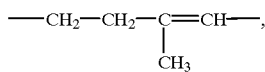

Z is —CH$_2$CH— or —CH=CH—; $R^2$ and $R^3$ are each H or each F; R, $R^1$ and $R^{1a}$ are OH or metal ions.

The disclosures of the above U.S. patents and U.S. patent applications are incorporated herein by reference.

In carrying out the method of the invention, a pharmaceutical composition will be employed containing at least one protein-prenyl transferase inhibitor in association with a pharmaceutical vehicle or diluent. The pharmaceutical composition can be formulated employing conventional solid or liquid vehicles or diluents and pharmaceutical additives of a type appropriate to the mode of desired administration. The compounds can be administered to mammalian species including humans, monkeys, dogs, etc. by an oral route, for example, in the form of tablets, capsules, granules or powders, or they can be administered by a parenteral route in the form of injectable preparations. The dose for adults is preferably between 200 and 2,000 mg per day, which can be administered in a single dose or in the form of individual doses from 1–4 times per day.

A typical capsule for oral administration contains protein-prenyl transferase inhibitor (250 mg), lactose (75 mg) and magnesium stearate (15 mg). The mixture is passed through a 60 mesh sieve and packed into a No. 1 gelatin capsule.

A typical injectable preparation is produced by aseptically placing 250 mg of sterile protein-prenyl transferase inhibitor into a vial, aseptically freeze-drying and sealing. For use, the contents of the vial are mixed with 2 mL of physiological saline, to produce an injectable preparation.

What is claimed is:

1. A method for treating and/or preventing ras-related tumors, which comprises administering to a mammalian species in need of treatment an anti-tumor effective amount of a phosphorus-containing protein-prenyl transferase inhibitor.

2. A method for treating and/or preventing ras-related tumors, which comprises administering to a mammalian species in need of treatment an anti-tumor effective amount of a phosphonate-containing protein-prenyl transferase inhibitor.

3. A method for blocking the farnesylation of ras oncogene products which comprises administering to a mammalian species in need of treatment a therapeutically effective amount of a phosphorus-containing protein-prenyl transferase inhibitor.

4. The method as defined in claim 1 wherein the protein-prenyl transferase inhibitor has the structure

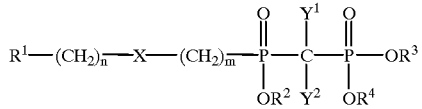

wherein m is 0, 1, 2 or 3; n is 0, 1, 2, 3 or 4;

$Y^1$ and $Y^2$ are H or halogen;

$R^2$, $R^3$ and $R^4$ may be the same or different and are independently H, metal ion, $C_1$ to $C_8$ alkyl or $C_3$ to $C_{12}$ alkenyl;

X is O, S, NH or —NCH$_2$R$^{15}$ wherein $R^{15}$ is H or $C_1$ to $C_5$ alkyl; and $R^1$ is $R^5$—$Q^1$—$Q^2$—$Q^3$— wherein $Q^1$, $Q^2$ and $Q^3$ are the same or different and are independently

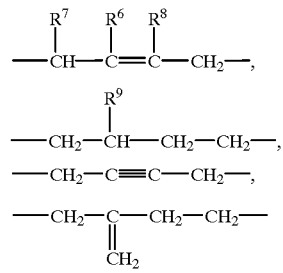

or a single bond, with the proviso that if $Q^1$ is a bond, then $Q^2$ and $Q^3$ are bonds, and if $Q^2$ is a bond then $Q^3$ is a bond, and wherein $R^6$ is H, lower alkyl or lower alkylthio; $R^8$ is H, halogen, trimethylsilyl or lower alkyl; and $R^9$ is H or lower alkyl;

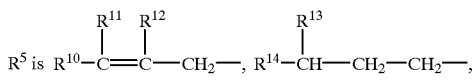

-continued $$CH_3-\underset{\underset{CH_2}{\|}}{C}-CH_2-CH_2-, CH_3(CH_2)_p$$

where p is an integer from 2 to 7, or $R^{16}-C\equiv C-CH_2-$ where $R^{16}$ is H or lower alkyl; $R^{10}$ and $R^{11}$ are the same of different and are independently H, lower alkyl, haloalkyl, halogen or lower alkenyl or $R^{10}$ and $R^{11}$ can be taken together to form $(CH_2)_s$ where s is an integer from 2 to 7; $R^{12}$ is H, lower alkyl, halogen or lower alkenyl; and $R^{13}$ and $R^{14}$ are the same or different and are independently lower alkyl; with the proviso that if all of $Q^1$, $Q^2$ and $Q^3$ are bonds, then $R^{10}$ and $R^{11}$ cannot both be H, and $R^5$ cannot be $CH_3(CH_2)_p$— with p less than or equal to 4, and when m is o, X is other than S; and if m is o and X is O, then n is 1, 2, 3 or 4; and including all stereoisomers thereof.

5. The method as defined in claim 4 wherein $R^5$ is $$R^{10}-\underset{\underset{}{\overset{R^{11}}{|}}}{C}=\underset{\underset{}{\overset{R^{12}}{|}}}{C}-CH_2-,$$

$Q^1$ is $$-\underset{\underset{}{\overset{R^7}{|}}}{CH}-\underset{\underset{}{\overset{R^6}{|}}}{C}=\underset{\underset{}{\overset{R^8}{|}}}{C}-CH_2-$$

and $Q^2$ is the same as or different from $Q^1$ and is $$-\underset{\underset{}{\overset{R^7}{|}}}{CH}-\underset{\underset{}{\overset{R^6}{|}}}{C}=\underset{\underset{}{\overset{R^8}{|}}}{C}-CH_2-,$$

and $Q^3$ is a bond, X is O or NH, n is 0, m is 1, $Y^1$ and $Y^2$ are H.

6. The method as defined in claim 1 wherein the protein-prenyl transferase inhibitor has the structure $$CH_3-\underset{\underset{CH_3}{|}}{C}=CH-CH_2-CH_2-\underset{\underset{CH_3}{|}}{C}=CH-CH_2-Q-(CH_2)_{\overline{n}}-X-\underset{\underset{OR^2}{|}}{\overset{\overset{O}{\|}}{P}}-\underset{\underset{Y^2}{|}}{\overset{\overset{Y^1}{|}}{C}}-\underset{\underset{OR^4}{|}}{\overset{\overset{O}{\|}}{P}}-OR^3$$

wherein Q is $$-CH_2-\underset{\underset{CH_3}{|}}{C}=CH-CH_2-$$

or a bond;
n is 0 to 4;
X is O, —NH— or $NCH_2R^{15}$;
$R^2$, $R^3$ and $R^4$ are the same or different and are H, lower alkyl, lower alkenyl, or a metal ion;
$Y^1$ and $Y^2$ may be the same or different and are H or halogen; and
$R^{15}$ is H or lower alkyl;
with the proviso that when X is O, n is 1, 2, 3, or 4.

7. The method as defined in claim 1 wherein the protein-prenyl transferase inhibitor is a bisphosphonate.

8. The method as defined in claim 1 wherein the protein-prenyl transferase inhibitor has the structure $$R^1-(CH_2)_{\overline{n}}-X-(CH_2)_{\overline{m}}-\underset{\underset{OR^2}{|}}{\overset{\overset{O}{\|}}{P}}-\underset{\underset{Y^2}{|}}{\overset{\overset{Y^1}{|}}{C}}-\underset{\underset{OR^4}{|}}{\overset{\overset{O}{\|}}{P}}-OR^3$$

wherein m is 1, 2 or 3; n is 0, 1, 2, 3 or 4;

$Y^1$ and $Y^2$ are H or halogen;

$R^2$, $R^3$ and $R^4$ may be the same or different and are independently H, metal ion, $C_1$ to $C_{12}$ alkenyl;

X is O, S, NH or $-NCH_2R^{15}$ wherein $R^{15}$ is H or $C_1$ to $C_5$ alkyl; and $R^1$ is $R^5-Q^1-Q^2-Q^3-$ wherein $Q^1$, $Q^2$ and $Q^3$ are the same or different and are independently $$-\underset{\underset{}{\overset{R^7}{|}}}{CH}-\underset{\underset{}{\overset{R^6}{|}}}{C}=\underset{\underset{}{\overset{R^8}{|}}}{C}-CH_2-,$$

$$-CH_2-\underset{\underset{}{\overset{R^9}{|}}}{CH}-CH_2-CH_2-,$$

$$-CH_2-C\equiv C-CH_2-,$$

$$-CH_2-\underset{\underset{CH_2}{\|}}{C}-CH_2-CH_2-$$

or a single bond, with the proviso that if $Q^1$ is a bond, then $Q^2$ and $Q^3$ are bonds, and if $Q^2$ is a bond then $Q^3$ is a bond, and wherein $R^6$ is H, lower alkyl, halo or haloalkyl; $R^7$ is H, halogen, lower alkyl or lower alkylthio; $R^8$ is H, halogen, trimethylsilyl or lower alkyl; and $R^9$ is H or lower alkyl;

$R^5$ is $R^{10}-\underset{\underset{}{\overset{R^{11}}{|}}}{C}=\underset{\underset{}{\overset{R^{12}}{|}}}{C}-CH_2-$, $R^{14}-\underset{\underset{}{\overset{R^{13}}{|}}}{CH}-CH_2-CH_2-,$ $$CH_3-\underset{\underset{CH_2}{\|}}{C}-CH_2-CH_2-, CH_3(CH_2)_p$$

where p is an integer from 2 to 7, or $R^{16}-C\equiv C-CH_2-$ where $R^{16}$ is H or lower alkyl; $R^{10}$, and $R^{11}$ are the same or different and are independently H, lower alkyl, haloalkyl, halogen or lower alkenyl or $R^{10}$ and $R^{11}$ can be taken together to form $(CH_2)_s$ where s is an integer from 2 to 7; $R^{12}$ is H, lower alkyl, halogen or lower alkenyl; and $R^{13}$ and $R^{14}$ are the same or different and are independently lower alkyl; with the proviso that if all of $Q^1$, $Q^2$ and $Q^3$ are bonds, then both $R^{10}$ and $R^{11}$ cannot be H, and $R^5$ cannot be $CH_3(CH_2)_p$— with a p less than or equal to 4, and including all stereoisomers thereof.

9. The method as defined in claim 8 wherein X is O, $Y^1$ and $Y^2$ are each F or H, m is 1 or 2 and n is 0 or 1 and $R^1$ is $R^5$—$Q^1$–$Q^2$ wherein $Q^1$ and $Q^2$ are other than a single bond.

10. The method as defined in claim 8 wherein $R^5$ is

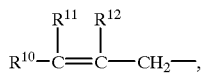

$Q^1$ is

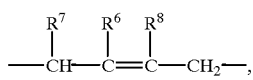

$Q^2$ is —$CH_2$—C≡C—$CH_2$—, and $Q^3$ is a bond.

11. The method as defined in claim 8 wherein $R^5$ is $CH_3(CH_2)_p$—, $Q^1$ is

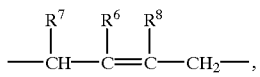

and $Q^2$ is the same as or different from $Q^1$ and is

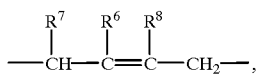

$Q^3$ is a bond.

12. The method as defined in claim 8 wherein $R^5$ is

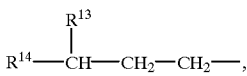

$Q^1$ is

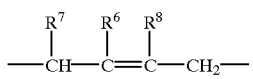

and $Q^2$ is the same as or different from $Q^1$ and is

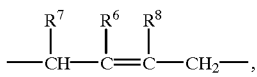

and $Q^3$ is a bond.

13. The method as defined in claim 1 wherein the prenyl-protein transferase inhibitor has the structure

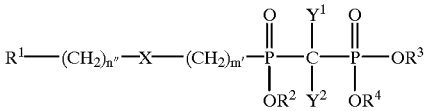

wherein m' is 1, 2 or 3; n" is 0, 1, 2 or 3;
$Y^1$ and $Y^2$ are H or halogen;
$R^2$, $R^3$ and $R^4$ may be the same or different and are independently H, metal ion, $C_1$ to $C_8$ alkyl or $C_3$ to $C_{12}$ alkenyl;
X is O, S, NH or —$NCH_2R^{15}$ wherein $R^{15}$ is H or $C_1$ to $C_5$ alkyl; and
$R^1$ is $R^5$—$Q^1$—$Q^2$—$Q^3$— wherein $Q^1$, $Q^2$ and $Q^3$ are the same or different and are independently

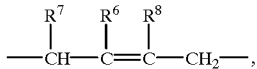

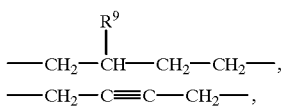

or a single bond, with the proviso that if $Q^1$ is a bond, then $Q^2$ and $Q^3$ are bonds, and if $Q^2$ is a bond then $Q^3$ is a bond, and wherein $R^6$ is H, lower alkyl, halo or haloalkyl; $R^7$ is H, halogen, lower alkyl or lower alkylthio; $R^8$ is H, halogen, trimethylsilyl or lower alkyl; and $R^9$ is H lower alkyl;
$R^5$ is

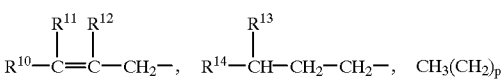

where p is an integer from 2 to 7, or $R^{16}$—C≡C—$CH_2$— where $R^{16}$ is H or lower alkyl; $R^{10}$, and $R^{11}$ are the same or different and are independently H, lower alkyl, haloalkyl, halogen or lower alkenyl or $R^{10}$ and $R^{11}$ can be taken together to form $(CH_2)_s$ where s is an integer from 2 to 7; $R^{12}$ is H, lower alkyl, halogen or lower alkenyl; and $R^{13}$ and $R^{14}$ are the same or different and are independently lower alkyl; with the proviso that if all of $Q^1$, $Q^2$ and $Q^3$ are bonds, then both $R^{10}$ and $R^{11}$ cannot be H, and $R^5$ cannot be $CH_3(CH_2)_p$— with a p less than or equal to 4, and including all stereoisomers thereof.

14. The method as defined in claim 8 wherein the protein-prenyl transferase inhibitor has the structure

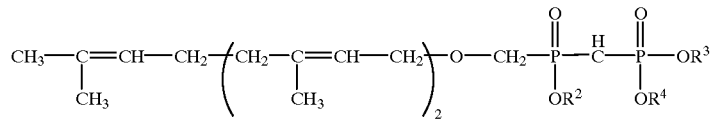

* * * * *